United States Patent
Pratap et al.

(10) Patent No.: US 7,183,291 B2
(45) Date of Patent: Feb. 27, 2007

(54) METHOD FOR THE TREATMENT OF MALARIA BY THE USE OF PRIMAQUINE DERIVATIVE $N^1$-(3-ETHYLIDINOTETRAHYDROFURAN-2-ONE)-$N^4$-(6-METHOXY-8-QUINOLINYL)-1,4-PENTANEDIAMINE AS GAMETOCYTOCIDAL AGENT

(75) Inventors: Ram Pratap, Lucknow (IN); Amiya Prasad Bhaduri, Lucknow (IN); Harsh Pati Thapliyal, Lucknow (IN); Sunil Kumar Puri, Lucknow (IN); Guru Prasad Dutta, Lucknow (IN); Anil Kumar Dwivedi, Lucknow (IN); Satyawan Singh, Lucknow (IN); Pratima Srivastava, Lucknow (IN); Vikash Chandra Pandey, Lucknow (IN); Sudhir Srivastava, Lucknow (IN); Shio Kumar Singh, Lucknow (IN); Ram Chandra Gupta, Lucknow (IN); Jagdishwar Sahai Srivastava, Lucknow (IN); Omkar Prasad Asthana, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/316,313

(22) Filed: May 21, 1999

(65) Prior Publication Data
US 2003/0199697 A1    Oct. 23, 2003

(30) Foreign Application Priority Data
Apr. 29, 1999    (IN)    ............... 655/DEL/99

(51) Int. Cl.
*C07D 215/38*    (2006.01)
*A61K 31/4709*    (2006.01)

(52) U.S. Cl. .................... 514/314; 546/171
(58) Field of Classification Search ........ 546/171; 514/314
See application file for complete search history.

(56) References Cited

U.S. PATENT DOCUMENTS 2,187,847 A * 1/1940 Andersag ............... 260/344
5,104,885 A * 4/1992 Nodiff ..................... 514/314

OTHER PUBLICATIONS

Bhat B et al. Indian J. Chem. Sect. B (1981), 20B(8), 703-5.*
Puri et al. Am. J. Trop. Med. Hyg., 1989, 41(6):638-642.*
Puri et al., Methemoglobin Toxicity and Hematological Studies on Malaria Anti-Relapse Compound CDRI 80/53 in Dogs, Am. J. Trop. Med Hyg., 41(6):638-642 (1989).*
Saxena ,N. et al."Effect of a new 8-Aminoquinoline Antimalarial compound on Hepatic . . . " Indian Journal of Medical Research Section A Infectious Diseases, Sep. 1989 (330-333).
Paliwal, J.K. et al. "Simultaneous determination of a new Antimalarial agent . . . " Journal of Chromatography, (1993) pp. 155-160.
Olliaro P.L. et al. "Status of Antimalarial drugs under development." Bulletin of the World Health Organization, (1995) pp. 565-571.

* cited by examiner

*Primary Examiner*—Celia Chang
*Assistant Examiner*—R. James Balls
(74) *Attorney, Agent, or Firm*—Ladas and Parry LLP

(57) ABSTRACT

The present invention a novel use of primaquine derivative $N^1$-(3-ethylidinotetrahydrofuran-2-one)-$N^4$-(6-methoxy-8-quinolinyl)-1,4-pentanediamine in the treatment and controlling the spread of malaria. In particular, the present invention discloses a method of treatment of malaria by the use of primaquine derivative $N^1$-(3-ethylidinotetrahydrofuran-2-one)-$N^4$-(6-methoxy-8-quinolinyl)-1,4-pentanediamine as a gametocytocidal agent.

7 Claims, No Drawings

METHOD FOR THE TREATMENT OF MALARIA BY THE USE OF PRIMAQUINE DERIVATIVE N$^1$-(3-ETHYLIDINOTETRAHYDROFURAN-2-ONE)-N$^4$- (6-METHOXY-8-QUINOLINYL)-1,4-PENTANEDIAMINE AS GAMETOCYTOCIDAL AGENT

FIELD OF THE INVENTION

The present invention relates to a method of treatment of malaria by the use of primaquine derivative N$^1$-(3-ethylidinoterahydrofuran-2-one)-N$^4$-(6-methoxy-8-quinolinyl)-1,4-pentanediamine as a gametocytocidal agent. More particularly, this invention relates to the use of primaquine derivative N$^1$-(3-ethylidinotetrahydrofuran-2-one)-N$^4$-(6-methoxy-8-quinolinyl)-1,4-pentanediamine of formula 1 shown below useful for controlling the spread of malaria by virtue of its high therapeutic value as a gametocytocidal agent.

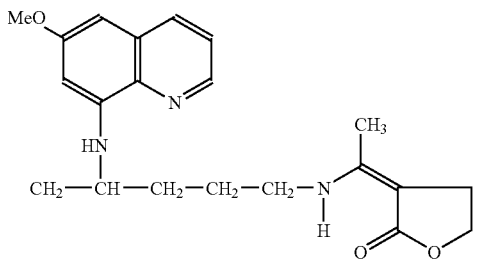

(1)

The primaquine derivative of the present invention does not damage either normal or G-6PD deficient erythrocytes to the extent it is observed with the use of primaquine.

BACKGROUND OF THE INVENTION

Malaria is one of the most serious protozoal infections in man. According to estimation made in the 90's, about 300 to 500 million people develop clinical infection and one million die of severe infection every year. India is also among the countries to have endemic regions of the disease. It is, therefore, of prime concern and requirement to have therapeutically safe agents for multiple use, especially those that block transmission of malaria through the individuals visiting endemic regions. A recent report of resurgence of malaria after a long gap of 40 years from Italy through transmission, highlights our concern [The Lancet, 350, 717 (1997)].

Malaria is caused by infection with any one of the four species of *Plasmodia*. The life cycle of *Plasmodia* is complex and comprises a sexual phase (called sporogyny) in the mosquito (a vector) and an asexual division (called schizogyny) in humans. The life cycle starts after injection of sporozoites by the bite of an infected female *anopheline* mosquito. Sporozoites then rapidly enter into liver parenchymal cells where they undergo exoerythrocytic schizogony forming exoerythrocytic stage of tissue schizonts which mature and release thousands of merozoites in the bloodstream upon the rupture of infected cell. Some of these merozoites enter erythrocytes where they transform into trophozoites and schizonts. The mature schizonts rupture and release merozoites into the circulation, which can infect other erythrocytes. This is termed as asexual schizogony (erythrocytic cycle) and it is this periodic release of merozoites which is responsible for characteristic periodicity of the fever in malaria. After several erythrocytic cycles, some erythrocytic forms differentiate into sexual forms called gametocytes. In *P. vivar.* and *P. ovale* infections, some of the sporozoites after entering the liver cells are known to remain dormant and form the latent tissue stage called hypnozoites. These hypnozoites upon activation develop secondary tissue schizonts, which are responsible for the recurrence of malaria called relapsing malaria. The 8-aminoquinoline antimalarial drugs of which primaquine (PQ) is of exceptional importance, have been demonstrated to possess activity against several life cycle stages of the parasite. These agents are active against the primary tissue schizonts, thus functioning as causal-prophylactic agents, against the secondary exoerythrocytic forms and curing relapsing forms of malaria. The transmission of malaria as discussed earlier, is through the injection of sporozoites by the bite of mosquitoes. These sporozoites develop in the mosquito feeding on an individual carrying mature gametocytes. The male and female gametocytes upon ingestion by a female *anopheline* mosquito fertilize and transform into zygote and ookinete stages. The ookinetes pierce through the epithelium of the midgut where it rounds up into the oocyst. A single oocyst contains as many as 10000 sporozoites. Primaquine has no sporontocidal activity when provided directly to the insects but has strong gametocytocidal activity and even stops transmission of resistant isolates when mosquitoes are fed on infected blood from primaquine treated animals. Thus, primaquine is also a strong transmission blocking agent. However, primaquine even being associated with radical curative and gametocytocidal activities is not in use as a prophylactic agent.

The practical problems associated with use of 8-aminoquinolines are mainly related to their toxicity because of prolonged use in radical treatment required due to fast metabolism of the drug. Primaquine is known to induce hemolytic lesions in patients suffering from a deficiency in glucose-6-phosphate-dehydrogenase (G-6PD), a genetic condition common among inhabitants in regions where malaria is endemic. Anemia is a common complication of hemolysis. Primaquine produces metabolites like o-quinone and p-quinomine functionalities, which because of their oxidative nature, oxidise unsaturated fatty acid of erythrocytes causing red blood cell (RBC) lysis. The reduced glutathione (GSH) controls the level of oxidative metabolites and the level of GSH is maintained through NADPH controlled GSSG reduction. NADPH is regulated by G-6PD and hence G-6PD deficient patients are more liable to RBC lysis. Primaquine is the only antimalarial drug, which inhibits the development of the parasite by interfering at several stages of the parasitic life cycle and therefore an ideal molecule for structural modification to provide a molecule with radical curative and gametocytocidal activities with low toxicity The study of the fate of primaquine, its metabolites and toxic manifestation in relation with metabolites will therefore, guide the direction of changes in the new molecule. A brief discussion of primaquine metabolism is given here.

Following oral administration of labelled primaquine it was found that 45% of the radioactivity was found in liver tissue, and 22% in the lung, adrenal, spleen, kidney, heart, blood and pancreas while 25% reached in to the plasma. Thus, primaquine is fairly well absorbed and only a small portion actually reaches the plasma.

Primaquine metabolism occurs at two sites of the molecule: one in the aromatic region at 5- and 6-positions and the other at 8-N aminoalkyl side chain. The first metabolic pathway leads to the formation of 5-hydroxyprimaquine (5-HPQ, 3), 5-hydroxy-demthyl primaquine (5-HDPQ) of the formula (4).

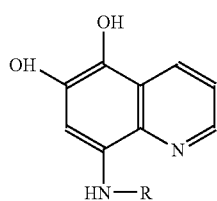

(4)

The second pathway originally observed to occur in the microorganisms, affects the 8-N-aminoalkyl chain and results in the formation of N-acetylprimaquine and desamino carboxylic acid of the Formula (12).

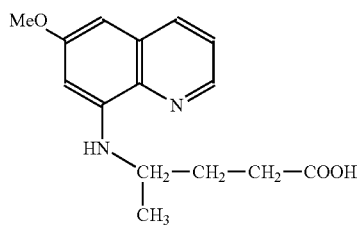

(12)

The carboxylic acid derivative is the major metabolite of primaquine in the human plasma.

Strother et al identified identified metabolites from the urine of primaquine treated dogs as 5-hydroxy-6-methoxy-8-(4-amino-1-methylbutylamino) quinoline of the Formula (3), desmethyl-6-hydroxy-8-(4-amino-1-methylbutylamino) quinoline of the Formula (9) and 5,6-dihydroxy-6-methoxy-8-(4-amino-1-methylbutylamino) quinoline of the Formula (4) shown below: [A. Strother, et al, 'Metabolism of *-amonoquinoline antimalarial agents'. Bulletin of the World Health organisation, 59, 413–425 (1981)].

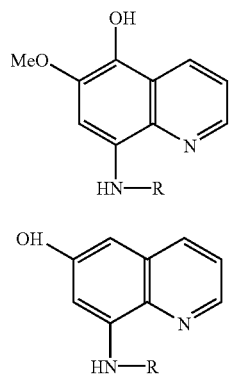

(3)

(9)

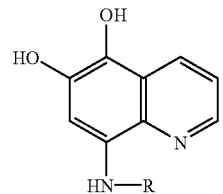

(4)

Among N-dealkylated derivatives of primaquine metabolites were identified as 6-methoxy-8-aminoquinoline of formula (10) [J. D. Baty et al 'The identification of 6-methoxy-8-aminoquinoline as a metabolite of primaquine in Man'. Biomedical Mass Spectrometry, 2, 304–306 (1975)] and 8-(3-carboxy-1-methylpropylamino)-6-methoxy quinoline of formula (12) shown below. [J. K. Baker, et al 'HPLC analysis of the metabolism of primaquine and the identification of a New Mammalian Metabolite' Journal of Chromatography, 230, 69–77 (1982)].

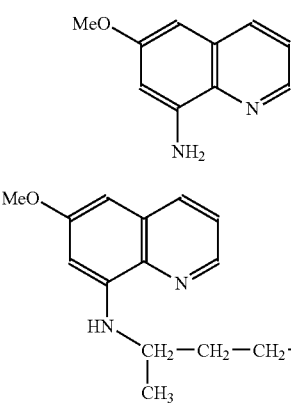

(10)

(12)

A blue colour metabolite derived from 5-hydroxy-desmethylprimaquine was identified as tricyclic quinomine of formula (8) shown below [A. Strother et al 'Metabolism of Primaquine by various Animal species' in Primaquine: Pharmacokinetics, Metabolism, Toxicity and Activity, pp 27–48 (1984), John Wiley & Sons].

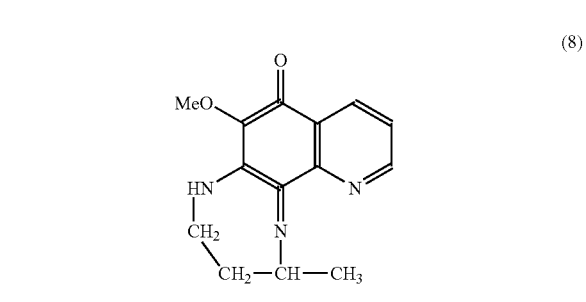

(8)

Therapeutic Activity of Primaquine and its Metabolites

Primaquine has blood schizontocidal activities whereas its desmethyl derivative has little. Two 5-OH derivatives of the formula of (3) and (4) shown above are highly active. The quinolines that lack the side chain of 8-position but have merely amino substituents shown in the formula (10) above and formula (11) below have no significant activity.

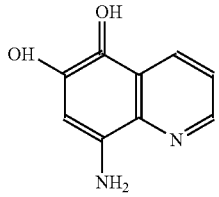

(11)

In marked contrast is the observation that the dealkylated derivatives of the formulae 10 and 11 retain their tissue schizontoidal effect. They are two to three times more active than primaquine.

The direct sporontocidal activity of PQ and of these putative metabolites is poor against the oocysts development when mosquitoes are fed on treated animals that supply the gametocytes. Primaquine is quite inactive as sporontocide when given directly to the insect, but is a very potent gametocytocidal agent.

The 5-hydroxy derivative of the formula (4) of desmethyl primaquine shows only a slight gametocytocidal activity. Desmethyl primaquine of the formula (5) shown below and 5-hydroxy of the formula (3) and carboxylic acid of the formula (12) metabolites of PQ are all inactive. Of particular interest is the observation that two of the quinolines of the formulae (10) and (11) shown above with unsubstituted —$NH_2$ group on 8-position are directly sporontocidal. [W. Peters et al, 'The activity of primaquine and its possible metabolites against rodent malaria' Primaquine: Pharmacokinetics, Metabolism, Toxicity and Activity, pp 93–101 (1984), John Wiley & Sons].

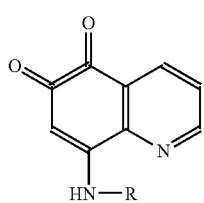

(5)

Toxicity of Primaquine and its Metabolites:

Primaquine of the formula (2) shown below itself appears to have little oxidant activity even when incubated with G-6PD deficient erythrocytes [I. M. Fraser et al, 'Effects of Drugs and Drug Metabolites on Erythrocytes from Normal and Glucose-6-phosphate Dehydrogenase Deficient Individuals', Annals of the New York Academy of Sciences, 151, 777–94 (1968)], John Wiley & Sons].

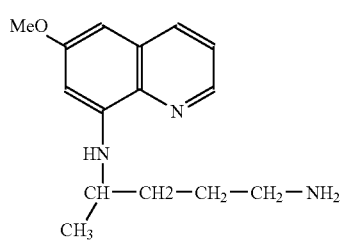

(2)

Whereas 5-hydroxyprimaquine of thr formula (3) and 5,6-dihydroxy-8-aminoquinoline of the formula (11) cause oxidation of oxyhemoglobin ($HbO_2$) to methemoglobin (Met Hb) and of reduced glutathione (GSH) [K. A. Fletcher et al, 'The Pharmacokinetics and Biochemical Pharmacology of Primaquine in Rhesus Monkeys and Rats' in Primaquine: Pharmacokinetics, Metabolism, Toxicity and Activity, pp 49–63 (1984), John Wiley & Sons].

The carboxylic acid of the formula (12), a major metabolite of primaquine circulating in the plasma, has not shown any antimalarial activity. It is uncertain whether it contributes significantly to the toxicity of primaquine although it does not cause methemoglobin formation in vitro. Earlier we reported causal prophylactic activity of primaquine derivative namely $N^1$-(3-acetyl-4,5-dihydro-2-furanyl)-$N^4$-(6-methoxy-8-quinolinyl)-1,4-pentanediamine at 3.16 mg/kg×3 doses against sporozoite induces P. cynomolgi B. infection in monkeys. The derivative also exerts anti-relapse (radical curative) activity at 1 mg/kg×7 days (G. P. Dutta, S. K. Puri, V. C. Pandey, M. Seth, A. P. Bhaduri, S. K. Chatterjee, O. P. Asthana and K. C. Gupta, Tropical Diseases, 286 (1998), G. P. Dutta, S. K. Puri, A. P. Bhaduri and M. Seth, Am. J. Trop. Med. Hyg. 41, 635, (1989). In the derivative, primaquine is substituted at primary amino functionality.

Thus from the above studies, it is obvious that primaquine possesses antimalarial activities such as blood schizontocidal, tissue schizontoidal and gametocytocidal which are also exhibited by its metabolites. Primaquine is even more active than its metabolites. The carboxylic acid of the formula (12) though a major metabolite, is non-functional. The metabolites of primaquine are also responsible for its toxicity. The tricyclic metabolite of the formula (8) is active but less toxic which therefore, suggests the significance of intact side chain. Therefore, if primaquine molecule is manipulated through the side chain possibly toxicity could be modulated. Secondly, primaquine is absorbed and metabolized very fast and as a consequence, oxidative burst accrues very fast. Therefore, its controlled delivery may result in less toxicity. This led us to prepare primaquine prodrug of less toxic profile. Primaquine is of a basic nature with a free amino functionality, which is a point of metabolism for inactive metabolite. We derivatised this amino functionality to enaminone and evaluated its efficacy for gametocytocidal action and methemoglobin toxicity. Enaminones are a functional group for controlled delivery of amino drugs. An enaminone derivative of a physiologically active amine may well show improved transport across biological membranes and allow a high concentration of the amine to be released close to the site of action. This functional group provides resistance towards hydrolytic cleavage at acidic pH as compared to the plain amine. We prepared enaminone derivative of primaquine shown in formula (1) on two accounts. Firstly, it should have slow metabolic degradation through side chain and secondly, compound of enhanced lipophilic character should penetrate better in the tissue, especially in the liver where hypnozoites reside. We therefore, embarked on the preparation of enaminone derivative of formula (1) and the results of its gametocytocidal effects and its safety profiles are mentioned here. As already mentioned earlier at the beginning, the search for a safe gametocytocidal agent is needed for two reasons, firstly, to block the recurrence of malaria in non-endemic regions where malaria has already been eradicated through vector control methods by individuals visiting endemic regions, and secondly, to block spread of even resistant strains.

Primaquine and its putative metabolites are shown below:

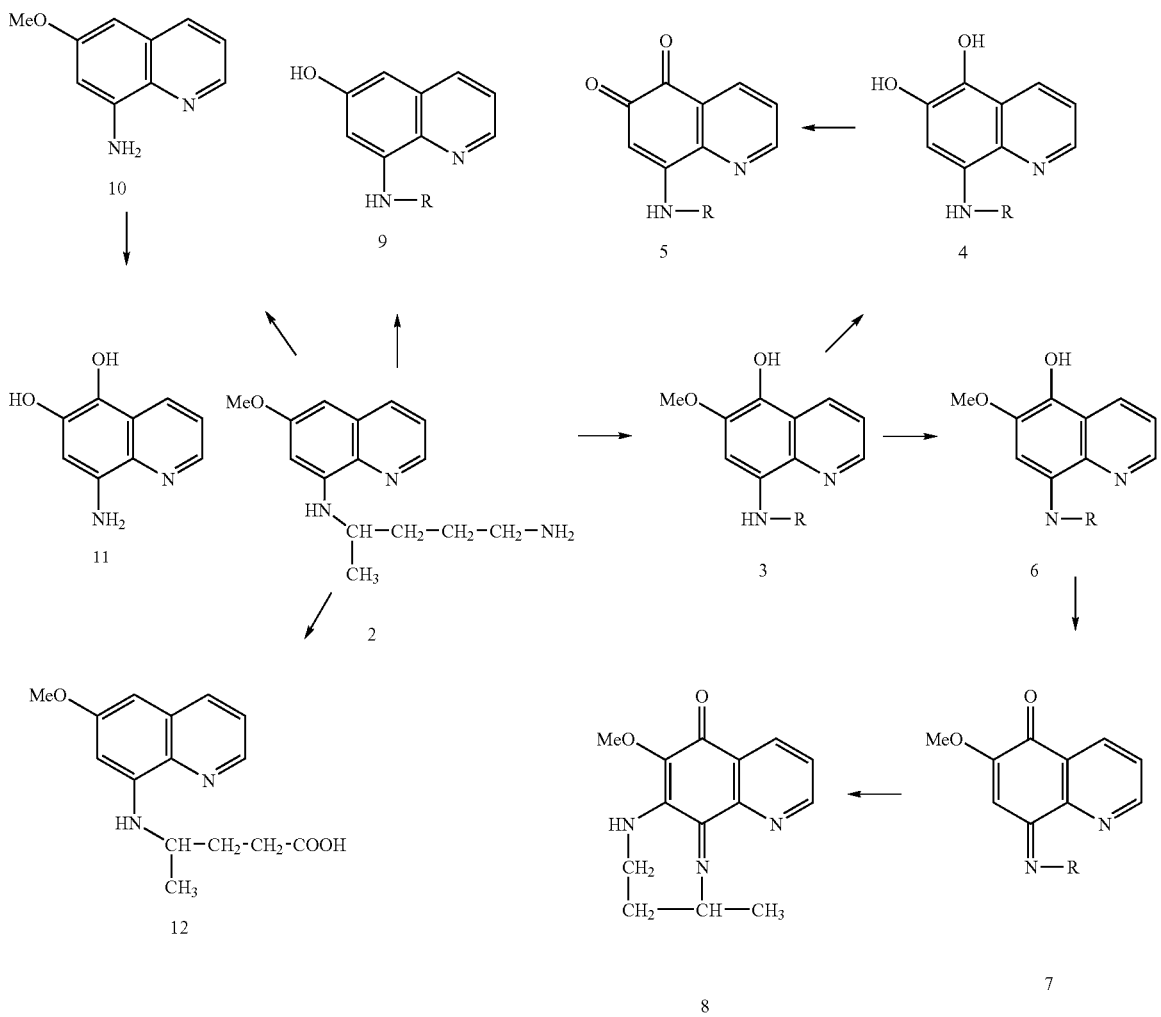

Primaquine and its putative metabolites

OBJECTS OF THE INVENTION

The main object of the invention is to provide a new primaquine derivative with the enaminone functionality having gametocytocidal activity and low toxicity for use as a transmission blocker.

Another object of the invention is to provide a new primaquine derivative for facilitating controlled delivery of amino drugs.

It is another object of the invention to provide a primaquine derivative having slow metabolic degradation through the side chain modification.

Another object of the invention is to provide a primaquine derivative with enaminone functional group providing resistance towards hydrolytic cleavage at acidic pH as compared to the plain enamine.

Another object of the invention is to provide a new primaquine derivative with enhanced lipophilic character to facilitate better penetration in the tissue especially in the liver where hypnozoites reside.

It is a further object of the invention to provide a new primaquine derivative with a high therapeutic index ratio in terms of methemoglobin formation.

Another object of the invention is to provide a primaquine derivative, which causes oxidation of glutathione (GSH) to a lesser extent.

It is yet another object of the invention to provide a process for the preparation of the novel primaquine derivative of formula (1).

It is a further object of the invention to provide for a method treatment of malaria using primaquine derivative $N^1$-(3-Ethylidinotetrahydrofuran-2-one)-$N^4$-(6-methoxy-8-quinolinyl)-1,4-pentanediamine as a gametocytocidal agent.

DETAILED DESCRIPTION OF THE INVENTION

The invention provides a method of treatment of malaria using a primaquine derivative of formula (1) shown below with the enaminone functionality having gametocytocidal activity and low toxicity as a transmission blocker. The method comprises administering to the animal, particularly human, infected with malaria, a compound of formula (1) or a pharmaceutical composition containing said compound of formula (1).

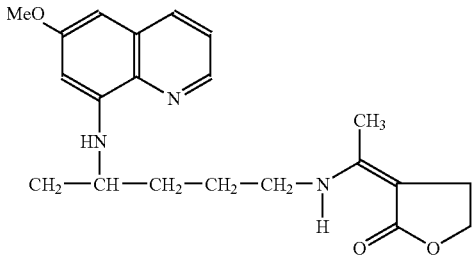

(1)

In another embodiment, the invention relates to a method of treatment of malaria using a new primaquine derivative for facilitating controlled delivery of amino drugs.

In a further embodiment, the invention relates to a method of treatment of malaria using a primaquine derivative having slow metabolic degradation through the side chain modification.

In yet another embodiment, the invention relates to a method of treatment of malaria using a primaquine derivative with enaminone functional group providing resistance towards hydrolytic cleavage at acidic pH as compared to the plain enamine.

In another embodiment, the present invention relates to a method of treatment of malaria using a primaquine derivative with enhanced lipophilic character to facilitate better penetration in the tissue especially in the liver where hypnozoites reside.

In another embodiment, the present invention relates to a method of treatment of malaria using a primaquine derivative with a high therapeutic index ratio in terms of methemoglobin formation.

In another embodiment, the present invention relates to a method of treatment of malaria using a primaquine derivative which causes oxidation of glutathione (GSH) to a lesser extent.

In another embodiment, the present invention relates to a process for the preparation of the primaquine derivative of formula (1).

In a further embodiment, the present invention relates to a method of treatment of malaria using primaquine derivative $N^1$-(3-Ethylidinotetrahydrofuran-2-one)-$N^4$-(6-methoxy-8-quinolinyl)-1,4-pentanediamine as a gametocytocidal agent.

The process for the preparation of primaquine derivative used in the present comprises the synthesis of enaminone: $N^1$-(3-ethylidinotetrahydrofuran-2-one)-$N^4$-(6-methoxy-8-quinolinyl)-1,4-pentanediamine by reaction of 8-(4-amino-1-methylbutylamino)-6-methoxy quinoline (primaquine) with 3-acetyl-τ-butyrolactone in presence of a base in catalytic amount. The reaction may be represented by the following scheme:

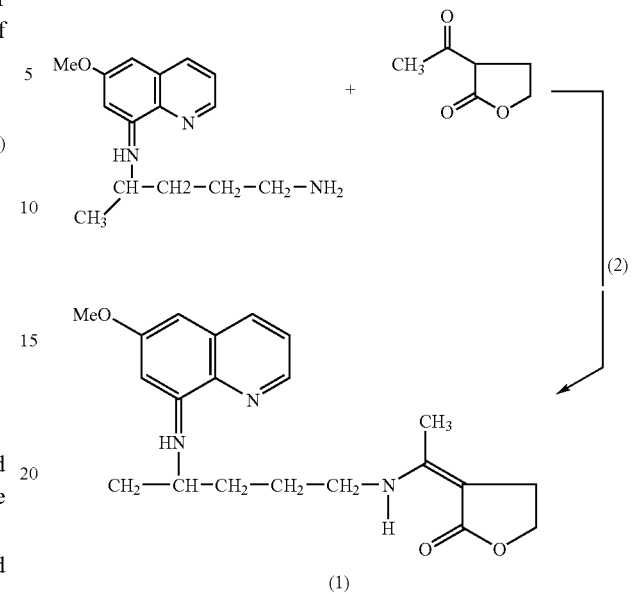

The following example illustrates the details of the process of this invention:

$N^1$-(3-ethylidinotetrahydrofuran-2-one)-$N^4$-(6-methoxy-8-quinolinyl)-1,4-pentanediamine A mixture of primaquine base (0.97 g, 3.7 mmole) freshly distilled 3-acetyl-r-butyrolactone (1.0 g, 7.8 mmole) and a base like piperidine (2–3 drops) were stirred under magnetic stirrer at room temperature. In an hour or so the reaction mixture solidified. The product was titrated in ether and filtered to get the product. It was crystallised from alcoholic solvent like propanol. Yield 0.89 g, m.p. 118–120° C.

Gametocytocidal Activity

For the gametocytocidal test, batches of 3–4 day old An. Stephensi were allowed to feed on *P. cynomolgi* infected Rhesus monkeys at appropriate gametocytaemia level. One hour after the control (pretreatment) feeding, compound of formula 1 was administered to the monkeys at 0.63, 1.25, 1.87, 2.5, 3.75 and 5.0 mg/kg in a single dose by oral route. Post-treatment feeding of batches of healthy mosquitoes was done at different times (5–48 hours). Mosquitoes were maintained as 26±1° C. under optimal insectary conditions. The infectivity rate and the oocyst counts were recorded on day 8. Mosquitoes were further maintained in the insectary to record the formation of sporozoites and the absence of sporozoites in some of the batches was also ensured by inoculation of mosquito homogenates into native monkeys.

Results: The gametocytocidal activity of compound of formula (1) was evaluated in 16 Rhesus monkeys and the pre-treatment mosquito infectivity results for these monkeys shows that the oocyst number for different batches ranged from 13.77±9.51 to 125.77±62,89 and the percent infectivity varied from 42.55 to 100% (See Table 1). Sequential mosquito feedings on a monkey treated at 0.63 mg/kg dose showed significant reduction in oocyst number and the percent infectivity at +5 h and +24 h post-treatment compared to the corresponding control feedings at −1 hr. Salivary gland dissections of the mosquitoes from these batches on day 15 showed the presence of sporozoites, thus indicating that oocyst completed normal sporogenic development. No oocysts were observed over the midguts from mosquitoes fed at +48 hr. after drug administration nor were any sporozoites seen in their salivary glands.

Identical results were obtained in the efficacy tests at 1.25 mg/kg in 2/2 monkeys, at 1.87 mg/kg in 2/2 monkeys and at 2.5 mg/kg in 2/3 monkeys. The mosquito batches fed at 4–5 hr. post-treatment showed marked decrease in the oocyst numbers, though these oocysts were able to complete the sporogenic cycle as indicated by the presence of sporozoites in salivary glands on day 15–16. The mosquito batches fed on these monkeys at +24 hr. and +48 hr. did not develop any oocysts nor were any sporozoites demonstrable in their salivary glands.

The oocyst development was completely blocked in the mosquito batches (fed 4–5 hr as well as +24 hr post-treatment) in one of the three monkeys treated at 2.5 mg/kg, 5/5 monkeys treated at 3.75 mg/kg and 3/3 monkeys treated at 5.0 mg/kg dose. Moreover, the salivary gland dissections from these batches carried out between days 14–20 post infective blood meal also did not show any sporozoites. The asexual parasitaemia and gametocytaemia levels for different monkeys is also shown in Table 1. Although the gametocytes were persisting in circulation at +24 hr. and +48 hr. post-treatment, these gametocytes were not infective for An. Stephensi as indicated by the absence of oocysts. Mosquito batches fed on the vehicle control monkey at −1 hr, +24 hr., +48 hr. and +72 hr. showed consistently high percent infectivity and oocyst number in all the four batches.

Infectivity tests were carried out to ensure that there was no sporozoite development in the mosquito batches found negative for oocysts on day 8 following their feeding on drug treated monkeys. Homogenates of 40–50 mosquitoes each from 11 batches fed on gametocyte carrying monkeys treated with compound 1 at 1.87, 2.5, 3.75 and 5.00 mg base/kg were inoculated into native Rhesus monkeys. None of these 11 monkeys developed potency up to 60 days of observations, indicating complete absence of any viable sporozoites in these batches (Table 1). Similar inoculations made from three pre-treatment (control) batches and one post-treatment batch (from vehicle control) resulted in the development of patent infection in three monkeys on day 9, 10, 10.

A comparision of the mosquito infectivity in batches fed prior to drug administration and at varying intervals after administration of compound of formula (1) has shown drastic reduction of mosquito infectivity and oocyst development. This effect was found to be dose dependant as complete inhibition was obtained at +48 hr. with 1.35–2.50 mg/kg at +24 hr. and the higher doses of 3.75 and 5.00 mg/kg rendered mature gametocytes non-infective to mosquitoes within 4–5 hours. This rapid decline of the mosquito infectivity is attributable to gametocytocidal action of drug. The persisting gametocytes circulating at 24–48 hr. post treatment in compound of formula (1) treated monkeys were non-infective to mosquitoes. Studies with primaquine have shown that 3.16 mg/kg dose produced complete gametocytocidal action at +24 hr. while at 1.00 mg/kg, nearly 98% loss of infectivity was observed (Table II). The completion of sporogonic cycle in 24–96 hr. old oocysts exposed to the action of compound of formula (1) at 10–50 mg/kg dose indicates absence of sporontocidal/oocysticidal action of the drug (Table III).

Methemoglobin Toxicity Studies

Comparision of Primaquine and Compound of Formula (1) in Relation to Their Effect on Methemoglobin Beagle dogs have been used for obtaining data on the methaemoglobin formation following treatment with compound of formula (1) or primaquine.

Colony bred beagle dogs were maintained in the kennel house of the Institute and fed with a standard diet. Fourteen dogs were divided into five experimental groups as detailed below:

Group I: Three dogs
  Primaquine @ 1.0 mg/kg (base)×7 days
Group II: Three dogs
  Primaquine @ 3.0 mg/kg (base)×7 days
Group III: Three dogs
  Compound of formula (1) @ 1.25 mg/kg (base)×7 days
Group IV: Three dogs
  Compound of formula (1) @ 3.75 mg/kg (base0×7days Primaquine or compound of formula (1) as the case may be was suspended in 0.3% methyl cellulose solution and administered orally in 10 ml. volume via catheter followed by 5 ml. water to flush the catheter. Treatment was administered once daily for seven doses (day 0–6), the day of the first dose being day 0. The animals were observed for 20–30 minutes for any vomitting. 5 ml. blood was collected from beagle dogs on day 0, 3, 7, 13 and 25 using potassium-oxalate crystals as anticoagulant. All the estimations/tests were conducted on the same day of collection of blood. Methaemoglobin was assayed by the method of Evelyn and Malloy (1938, J. Biol. Chem., 126, 655–662). These values are recorded in Table V. At primaquine antirelapse curative dosage against *P. cynomolgi* in monkeys, (Group I, 1.0 mg/kg), the mean Met-Hb values increased by 3.7 fold on day 7. There was then a gradual decline in Met-Hb values by day 25, but the level was still 2.0 fold the pretreatment level. Primaquine administered at three times the curative dose (Group II, 3.0 mg/kg) showed 10.5 fold increase over the corresponding day 0 value, and the elevated levels again declined after treatment and were 2.5 fold higher than pretreatment values on day 25. Compound 1 at curative dose (Group III: 1.25 mg/kg) only marginally increased the Met-Hb values by 1.7 fold on day 7 and slight increase (2.4 fold) over the pretreatment values on day 25. At the higher dose (Group IV: 3.75 mg/kg) the Met-Hb level on day 7 increased by 3.2 fold and the values declined to 1.8 fold of pretreatment values on day 25. The Vehicle Control Group (Group V) showed marginal fluctuation of Met-Hb level within the normal limits.

Thus on day 7 of the curative dose level, Met-Hb formation was 2.7 fold lower with test compound as compared to primaquine. Likewise, at three times the therapeutic dose, the Met-Hb formation with the test compound was 3.6 fold lower as compared to primaquine.

Reduced Glutathione (GSH) in Human Erythrocytes

Drug induced haemolysis is a serious complication in persons deficient in G-6-PD enzyme. The presence of reduced glutathione (GSH) in erythrocytes control the level of oxidative metabolites. Therefore, drugs, which cause lesser oxidation of GSH level are safe. The level of reduced glutathione in erythrocytes of healthy and G-6-PD deficient individuals were measured after incubation with PQ and compound of formula (1) and results are mentioned in Tables V and VI. G-6-PD deficiency was detected by the fluorescent spot screening test and confirmed by the enzyme assay method. Heparinised blood samples were collected from each individual and after centrifugation, the packed cells were washed three times with cold saline. One ml. aliquots of washed cells were then incubated with different concentrations of the drugs ranging from 1 to 5 µg/ml base of PQ diphosphate and equivalent doses ranging from 1.25 to 62.5 µg/ml of compound 1 in a water bath at 37° C. with occasional agitation for 3 hours. GSH levels were estimated by the method of Bentler et al [Improved Method for the Determination of Blood Glutathione, J. Lab. Clin. Med., 61, 882–888 (1963)].

RESULTS

Mean erythrocyte GSH levels in the controls (without drug) were significantly lower in the G-6-PD deficient individuals (29.5±1.86mg %) as compared to the normals (49.91±4.49 mg %).

Normal erythrocytes exposed to different doses of PQ showed a fall in GSH levels, which reached statistical significance at concentration 10 μg/ml., whereas the same incubated with compound 1 showed significant decrease in GSH levels only at concentration 31.25 μg/ml. (Table V).

At concentration of 25 μg/ml. and 50 μg/ml. of PQ and equivalent doses of compound of formula (1) in G-6-PD deficient erythrocytes, the decrease in GSH level was statistically significant ($P<0.001$) in cow when GSH level compared to GSH levels in other controls. However, the decrease in PQ treated erythrocytes was pronounced as compared to compound of formula (1) treated group, thus showing the higher safety margin of the new compound.

Percentage decrease in GSH levels was more pronounced in normal and G-6-PD deficient erythrocytes treated with PQ as compared to compound of formula (1). Statistically significant decreases were observed at concentrations of 25 μg/ml. and 50 μg/ml. of PQ as compared to the equivalent doses of test compounds in both normal and G-6-PD deficient erythrocytes (Tables V and VI).

TABLE I

Effect of single dose compound 1 on *P. cynomolgi* B gametocytes as determined by their infectivity to *An. stephensi* mosquitoes.

| Dose mg/kg at 0 hr. | Time of mosquito feeding | Parasitaemia/mm$^3$ Asexual | Gametocytes | No. of mosquitoes infected/dissected (% infectivity) | Oocyst No. per gut (Mean ± SD) |
|---|---|---|---|---|---|
| 0.63 | −1 hr | 48816 | 1728 | 27/30 (90.0) | 86.74 ± 39.2 |
|  | +5 hr |  |  | 23/51 (45.1) | 10.22 ± 6.8 |
|  | +24 hr | 30024 | 1404 | 15/46 (32.61) | 2.93 ± 2.4 |
|  | +48 hr | 23220 | 756 | 0/24 (0) | Nil |
| 1.25 | −1 hr | 126965 | 1895 | 34/38 (89.57) | 22.35 ± 11.8 |
|  | +5 hr |  |  | 12/57 (21.05) | 2.17 ± 1.7 |
|  | +24 hr | 103846 | 1516 | 0/36 (0) | Nil |
|  | +48 hr | 15914 | 109 | 0/24 (0) | Nil |
| 1.25 | −1 hr | 23712 | 1026 | 20/47 (42.55) | 14.40 ± 7.29 |
|  | +5 hr |  |  | 15/70 (21.43) | 2.60 ± 1.7 |
|  | +24 hr | 21204 | 486 | 0/30 (0) | Nil |
| 1.87 | −1 hr | 33602 | 1166 | 25/30 (83.33) | 28.20 ± 18.9 |
|  | +4 hr |  |  | 6/40 (15.00) | 1.17 ± 0.4 |
|  | +24 hr | 18020 | 530 | 0/27 (0) | Nil |
|  | +48 hr | 7208 | 212 | 0/24 (0) | Nil |
| 1.87 | −1 hr | 61560 | 1026 | 23/25 (92.0) | 80.69 ± 35.7 |
|  | +4 hr |  |  | 18/31 (58.06) | 13.00 ± 12.3 |
|  | +24 hr | 42180 | 798 | 0/38 (0) | Nil** |
|  | +48 hr | 5130 | 228 | 0/21 (0) | Nil |
| 2.50 | −1 hr | 33578 | 1442 | 36/46 (78.26) | 13.72 ± 9.5 |
|  | +4 hr |  |  | 20/33 (60.61) | 2.90 ± 2.2 |
|  | +24 hr | 45320 | 927 | 0/29 (0) | Nil |
|  | +48 hr | 18025 | 206 | 0/21 (0) | Nil |

TABLE I-continued

Effect of single dose compound 1 on *P. cynomolgi* B gametocytes as determined by their infectivity to *An. stephensi* mosquitoes.

| Dose mg/kg at 0 hr. | Time of mosquito feeding | Parasitaemia/mm$^3$ Asexual | Gametocytes | No. of mosquitoes infected/dissected (% infectivity) | Oocyst No. per gut (Mean ± SD) |
|---|---|---|---|---|---|
| 2.50 | −1 hr | 135464 | 4130 | 26/28 (92.86) | 125.77 ± 62.8 |
|  | +5 hr |  |  | 11/30 (36.67) | 4.64 ± 2.8 |
|  | +24 hr | 96642 | 2478 | 0/30 (0) | Nil |
| 2.50 | −1 hr | 38081 | 2147 | 29/37 (78.38) | 55.79 ± 41.0 |
|  | +5 hr |  |  | 0/33 (0) | Nil** |
|  | +24 hr | 31075 | 1243 | 0/44 (0) | Nil** |
| 3.75 | −1 hr | 55728 | 1296 | 26/27 (96.30) | 22.35 ± 15.8 |
|  | +4 hr |  |  | 0/25 (0) | Nil |
|  | +24 hr | 55808 | 540 | 0/28 (0) | Nil |
| 3.75 | −1 hr | 45796 | 1070 | 15/22 (68.18) | 22.00 ± 16.3 |
|  | +4 hr |  |  | 0/21 (0) | Nil |
|  | +24 hr | 25894 | 535 | 0/21 (0) | Nil |
| 3.75 | −1 hr | 68320 | 2318 | 33/40 (82.50) | 60.64 ± 35.4 |
|  | +5 hr |  |  | 0/30 (0) | Nil** |
|  | +24 hr | 26108 | 366 | 0/30 (0) | Nil** |
| 3.75 | −1 hr | 48336 | 954 | 22/22 (100.0) |  |
|  | +4 hr |  |  | 0/41 (0) |  |
|  | +24 hr | 65084 | 1696 | 0/27 (0) |  |

TABLE II

Gametocytocidal Activity of Primaquine

| Dose mg/kg at 0 hr | Time of mosquito feeding | Parasitaemia/mm$^3$ Asexual | Gametocytes | No. of mosquitoes infected/dissected (% infectivity) | oocyst no. per gut (Mean ± SD) |
|---|---|---|---|---|---|
| 1.00 mg/kg | −1 hr | 36166 | 1428 | 32/40 (80.0) | 17.13 ± 10.0 |
|  | +5 hr |  |  | 32/44 (72.7) | 13.69 ± 7.2 |
|  | +24 hr | 28048 | 526 | 0/55 (0) | Nil |
|  | +48 hr | 15332 | 234 | 0/40 (0) | Nil |
| 1.00 mg/kg | −1 hr | 42394 | 5152 | 25/34 (72.53) | 37.14 ± 16.6 |
|  | +5 hr |  |  | 36/46 (78.26) | 34.08 ± 14.7 |
|  | +24 hr | 26832 | 3256 | 3/45 (6.67) | 2.17 ± 1.7 |
|  | +48 hr | 12140 | 635 | 0/40 (0) | Nil |
| 3.16 mg/kg | −1 hr | 29680 | 1230 | 37/51 (72.55) | 57.59 ± 31.0 |
|  | +5 hr |  |  | 0/53 (0) | Nil |
|  | +24 hr | 23112 | 749 | 0/33 (0) | Nil |
| 3.16 mg/kg | −1 hr | 16824 | 1026 | 20/47 (42.55) | 24.4 ± 7.2 |
|  | +5 hr |  |  | 15/46 (32.61) | 2.6 ± 1.76 |
|  | +24 hr | 21204 | 670 | 0/43 (0) | Nil |

TABLE III

Effect of Compound 1 on developing oocysts of *P. cynomolgi An. stephensi* mosquitoes

| Age of Infection in mosquitoes | Mosquito feeding on drug treated*/control monkey | No. of mosquitoes infected/dissected (% infectivity) | oocyst number gut (Mean ± SD) |
|---|---|---|---|
| 24 hr | 10 mg/kg | 17/20 (85.00) | 144.47 ± 60.35 |
|  | Control | 15/18 (83.33) | 133.33 ± 62.30 |
|  | 50 mg/kg | 23/27 (85.19) | 67.00 ± 43.58 |
|  | Control | 29/36 (80.56) | 66.00 ± 43.48 |

TABLE III-continued

Effect of Compound 1 on developing oocysts of *P. cynomolgi An. stephensi* mosquitoes

| Age of Infection in mosquitoes | Mosquito feeding on drug treated*/ control monkey | Day 8 oocyst record | |
|---|---|---|---|
| | | No. of mosquitoes infected/dissect-ed (% infectivity) | oocyst number gut (Mean ± SD) |
| 48 hr | 10 mg/kg | 20/20 (100.0) | 133.20 ± 96.22 |
| | Control | 19/21 (90.48) | 124.05 ± 65.85 |
| | 50 mg/kg | 26/33 (78.79) | 46.15 ± 36.70 |
| | Control | 28/34 (82.35) | 42.57 ± 35.27 |
| 72 hr | 10 mg/kg | 22/25 (88.00) | 20.36 ± 17.81 |
| | Control | 23/28 (82.14) | 26.83 ± 19.00 |
| | 50 mg/kg | 25/29 (86.21) | 27.16 ± 20.60 |
| | Control | 22/32 (68.75) | 26.59 ± 22.05 |
| 96 hr | 50 mg/kg | 18/26 (69.23) | 40.33 ± 27.38 |
| | Control | 19/25 (76.00) | 47.42 ± 28.46 |

*Mosquitoes with 24–96 hr old oocysts were allowed to engorge blood from naive monkey administered compound 1 at −7 hr of the mosquito feeding
**Patent infection developed on days 9–10 in naive monkeys upon inoculation of 10 mosquitoes' homogenates.

TABLE IV

Methaemoglobin levels (g %) in Beagle dogs after treatment with Primaquine and compound 1.

| Group | Treatment | Day 0 | Day 3 | Day 7 | Day 13 | Day 25 |
|---|---|---|---|---|---|---|
| 1. | Primaquine 1.0 mg/kg | 0.65 ± 0.03 | 0.85 ± 0.13 | 02.39 ± 0.23 | 1.98 ± 0.34 | 1.33 ± 0.0 |
| 2. | Primaquine 1.0 mg/kg | 0.74 ± 0.07 | 1.94 ± 0.33 | 7.81 ± 1.48 | 5.51 ± 1.03 | 1.86 ± 0.0 |
| 3. | Compound 1 1.25 mg/kg | 0.53 ± 0.11 | 0.87 ± 0.17 | 0.89 ± 0.29 | 1.04 ± 0.07 | 1.26 ± 0.19 |
| 4. | Compound 1 3.75 mg/kg | 0.66 ± 0.15 | 1.0 ± 0.19 | 2.14 ± 0.89 | 1.66 ± 0.52 | 1.18 ± 0.14 |
| 5. | Compound 1 1.0 mg/kg | 0.64 ± 0.09 | 0.46 ± 0.09 | 0.74 ± 0.01 | 0.65 ± 0.10 | 0.83 ± 0.0 |

Day 0 = Start of drug treatment
Day 3 = After three doses
Day 7 = 1 day after last dose of drug
Day 13 = 7 days after last dose of drug
Day 25 = 19 days after last dose of drug

TABLE V

GSH levels in normal erythrocytes with different doses of primaquine and equivalent doses of compound 1.

| Primaquine | | Compound 1 | |
|---|---|---|---|
| Dose (μg/ml) | GSH (mg %) (Mean ± SE) | Dose (μg/ml) | GSH (mg %) Mean ± SE |
| Control (No drug) | 49.91 ± 4.49 | Control (No drug) | 49.91 ± 4.49 |
| 1.00 | 43.50 ± 5.70 | 1.25 | 44.08 ± 5.80 |
| 5.00 | 39.00 ± 6.16 | 6.25 | 42.50 ± 5.85 |
| 10.00 | 29.67 ± 6.49 | 12.50 | 38.25 ± 5.68 |
| 25.00 | 19.42 ± 2.83 | 31.25 | 31.00 ± 5.15* |
| 50.00 | 10.37 ± 1.57 | 62.50 | 32.75 ± 5.39* |

*Comparison of equivalent doses of compound 1 with primaquine
*P < 0.05
**P < 0.01

TABLE VI

GSH levels in G-6-PD deficient erythrocytes with different doses of primaquine and equivalent doses of compound 1.

| Primaquine | | Compound 1 | |
|---|---|---|---|
| Dose (μg/ml) | GSH (mg %) (Mean ± SE) | Dose (μg/ml) | GSH (mg %) Mean ± SE |
| Control (No drug) | 29.50 ± 1.86 | Control (No drug) | 29.50 ± 1.86 |
| 1.00 | 25.75 ± 2.17 | 1.25 | 26.04 ± 2.20 |
| 5.00 | 19.17 ± 1.50 | 6.25 | 23.42 ± 1.66 |
| 10.00 | 14.83 ± 1.89 | 12.50 | 20.00 ± 1.73 |
| 25.00 | 10.50 ± 1.52 | 31.25 | 17.17 ± 1.81* |
| 50.00 | 9.00 ± 1.94 | 62.50 | 16.62 ± 1.84* |

*P < 0.05. Comparison of compound 1 with primaquine

We claim:

1. A method for reducing malaria transmission from a malaria infected animal which comprises administering a therapeutically effective amount of a compound of the formula (1)

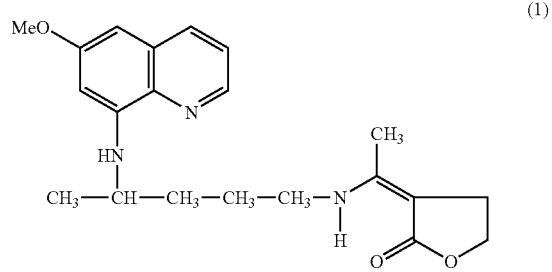

(1)

to the animal, said compound being administered once per seven days in an amount from 0.63 mg/kg of body weight to 5.00 mg/kg of body weight of animal.

2. A method according to claim 1, wherein the animal is a carrier of mature gametocytes of plasmodium species.

3. A method according to claim 2, wherein the animal is a human.

4. A method according to claim 1, wherein the amount is from 0.63 mg/kg of body weight to 3.75 mg/kg of body weight.

5. A method according to claim 1, wherein the amount is from 0.63 mg/kg of body weight to 2.5 mg/kg of body weight.

6. A method according to claim 1, wherein the amount is from 0.63 mg/kg of body weight to 1.87 mg/kg of body weight.

7. A method according to claim 1, wherein the amount is from 0.63 mg/kg of body weight to 1.25 mg/kg of body weight.

* * * * *